(12) United States Patent
Ford et al.

(10) Patent No.: US 9,727,936 B2
(45) Date of Patent: Aug. 8, 2017

(54) METHOD TO TRANSFORM CLINICIAN ORDER ENTRY

(75) Inventors: Daniel A. Ford, Mount Kisco, NY (US); Sondra R. Renly, Elmsford, NY (US)

(73) Assignee: International Business Machines Corporation, Armonk, NY (US)

(*) Notice: Subject to any disclaimer, the term of this patent is extended or adjusted under 35 U.S.C. 154(b) by 2205 days.

(21) Appl. No.: 12/633,832

(22) Filed: Dec. 9, 2009

(65) Prior Publication Data
US 2011/0137679 A1 Jun. 9, 2011

(51) Int. Cl.
*G06Q 50/00* (2012.01)
*G06Q 10/00* (2012.01)
(Continued)

(52) U.S. Cl.
CPC ............ *G06Q 50/22* (2013.01); *G06Q 10/10* (2013.01); *G06Q 50/24* (2013.01)

(58) Field of Classification Search
CPC .......... G06F 19/32; G06F 19/34; G06F 19/36; G06Q 50/22; G06Q 50/24
See application file for complete search history.

(56) References Cited

U.S. PATENT DOCUMENTS 5,772,585 A * 6/1998 Lavin .................... G06F 19/322 128/920
5,823,948 A * 10/1998 Ross et al. .................... 600/300
(Continued)

FOREIGN PATENT DOCUMENTS

JP H10143473 5/1998

OTHER PUBLICATIONS

Seng, et al., "Enhancing chronic disease management through telecare—the Singapore health services experience," Journal of Telemedicine and Telecare, J. Telemed. Telecare (UK), vol. 13, suppl.3, p. S3:73-6, 7th International Conference on Successes and Failures in Telehealth, Aug. 27-28, 2007, Australia.
(Continued)

*Primary Examiner* — Rachel L Porter
(74) *Attorney, Agent, or Firm* — Gibb & Riley, LLC

(57) ABSTRACT

A computer-implemented method receives, into a computerized system, routine electronic transmissions such as a clinician order entry (CPOE) order message relating to a patient. The order message is used to identify one of a number of pre-established templates to create an individualized wellness plan. The method identifies data variables that need to be supplied for the wellness plan and identifies patient documentation related to the wellness plan. The method supplies the data variables and combines patient documentation into the wellness plan. The method identifies and includes dependency-awareness of tasks, reminders, and appointments within and across wellness plans. The method can customize the wellness plan according to clinician preferences and patient preferences, and can restrict access and content of the wellness plan. The method provides the wellness plan to the patient through their preferred interactive calendar application and obtains the remaining data variables, performs across plan dependency checks, and obtains the patient preferences from the patient through the interactive calendar application. This allows the method to provide the patient a list of tasks, reminders, and appointments through the interactive calendar application and enables both clinician and patient to track plan progress and completion.

10 Claims, 4 Drawing Sheets

(51) Int. Cl.
G06Q 50/22 (2012.01)
G06Q 10/10 (2012.01)
G06Q 50/24 (2012.01)

(56) References Cited

U.S. PATENT DOCUMENTS

| | | | |
|---|---|---|---|
| 6,018,713 | A * | 1/2000 | Coli et al. .......................... 705/2 |
| 6,039,688 | A * | 3/2000 | Douglas et al. .............. 600/300 |
| 6,757,898 | B1 | 6/2004 | Ilsen et al. |
| 7,072,725 | B2 * | 7/2006 | Bristol et al. ................... 700/90 |
| 2002/0019749 | A1 | 2/2002 | Becker et al. |
| 2002/0062230 | A1 | 5/2002 | Morag et al. |
| 2003/0028399 | A1 | 2/2003 | Davis et al. |
| 2003/0120516 | A1 | 6/2003 | Perednia |
| 2004/0210458 | A1 | 10/2004 | Evans et al. |
| 2005/0102159 | A1 | 5/2005 | Mondshine |
| 2005/0108057 | A1 | 5/2005 | Cohen et al. |
| 2005/0187948 | A1 * | 8/2005 | Monitzer et al. ............. 707/100 |
| 2005/0283385 | A1 | 12/2005 | Hunkeler et al. |
| 2006/0031101 | A1 | 2/2006 | Ross |
| 2006/0136267 | A1 | 6/2006 | Brackett et al. |
| 2006/0277076 | A1 * | 12/2006 | Hasan et al. ...................... 705/3 |
| 2007/0174079 | A1 * | 7/2007 | Kraus .................... G06Q 10/10 705/3 |
| 2007/0198296 | A1 | 8/2007 | Pellinat et al. |
| 2008/0104104 | A1 * | 5/2008 | Nolan ............... G06F 17/30011 |
| 2008/0201168 | A1 | 8/2008 | Brown |
| 2008/0201174 | A1 | 8/2008 | Ramasubramanian et al. |

OTHER PUBLICATIONS

South Korea Prior Art Search Dated Sep. 20, 2016. pp. 1-2.

* cited by examiner

METHOD TO TRANSFORM CLINICIAN ORDER ENTRY

BACKGROUND

Field of the Invention

The embodiments of the invention generally relate to the creation of interactive temporal wellness plans from routine electronic transmissions such as clinician orders and scheduling events for patients and, more specifically, to a method and system for utilizing wellness plans in a dependency-aware calendar to facilitate medical compliance and interventions.

Description of the Related Art

A solid implementation of an automated transformation of routine electronic transmissions such as clinician orders and scheduling events for patient calendars attacks two persistent problems in the medical community. First, it creates new value for the clinician to utilize clinician order entry (CPOE) where adoption of CPOE greatly lags behind electronic record adoption. Order messages today are consumed by internal healthcare systems and pharmacies, which benefit from the clinician entering their own orders. Clinicians have identified far more drawbacks to CPOE than benefits. However, clinicians eventually adopt technology that either helps them or their patients.

Second, most acute care treatments (e.g., take antibiotic for 2 full weeks) or preventative care recommendations (e.g., flu shot clinic next week) are not verified, and only clinics with significant resources try to verify compliance in chronic patients (ex diabetics). Quality measurements exposed publicly through increased reporting requirements will increase the need for compliance analysis in the future.

SUMMARY

In view of these issues, the present embodiments provide a method and system of utilizing pre-established templates and an interactive user calendar to deliver new value from routine electronic transmissions. One embodiment herein comprises a computer-implemented method that receives, into a computerized system, a clinician order entry (CPOE) order relating to a patient. The order message is used to identify one of a number of pre-established templates to create an individualized wellness plan.

The method identifies data variables that need to be supplied for the wellness plan. The method supplies such data variables, using the computerized system, by searching databases for the data variables, receiving input from health care professionals for the data variables, and/or receiving input from the patient for the data variables.

The method also identifies patient documentation related to the wellness plan, using the computerized system. The patient documentation comprises medical decision support documentation, patient educational documentation, contra-indication checks documentation, etc. The method then combines the patient documentation into the wellness plan. The method can customize the wellness plan according to clinician preferences and patient preferences, and can restrict content of the wellness plan, using the computerized system. The method receives the clinician preferences from health care professionals and receives the patient preferences from the patient. The patient preferences can include choices regarding the type of interactive calendar application preferred by the patient. Further, the level of access restrictions to wellness plan content can be based on the type of interactive calendar application preferred by the patient.

The method identifies and includes dependency-awareness in the wellness plan. The method identifies dependencies, using the computerized system, by searching databases for conditions and contra-indications that could be identified within the wellness plan such as through data variables as well as across wellness plans added to the patient's interactive calendar application with content unknown to the clinician.

The method provides the wellness plan to the patient through their preferred interactive calendar application and obtains the remaining data variables and the patient preferences from the patient through the interactive calendar application, using the computerized system. This allows the method to provide the patient a list of tasks, reminders, and appointments through the interactive calendar application, using the computerized system.

To track the progress and completion of the wellness plan, the method receives feedback regarding completion of the tasks from the user, the treatment provider, the pharmacy, or other entities, again using the computerized system. Further, the method updates the interactive calendar based on the feedback and can output reports for clinicians and patients regarding the status of the wellness plan based on the interactive calendar application and the feedback (using the computerized system).

Exemplary system embodiments herein include a computerized system for processing clinician order entry (CPOE) orders. The system has at least one computerized storage medium operatively connected to at least one processor. The computerized storage medium stores a plurality of pre-established templates. Each of the templates comprises a wellness plan, and each wellness plan comprises temporal tasks, reminders, calendar appointments, etc.

Each of the pre-established templates further identifies patient documentation related to the wellness plan. The patient documentation comprises medical decision support documentation, patient educational documentation, contra-indication checks documentation, etc.

At least one interface is operatively connected to the processor. The interface receives routine electronic transmissions such as a CPOE order message relating to a patient. The order message is used to identify one of the pre-established templates to create an individualized wellness plan. The processor identifies data variables that need to be supplied for the wellness plan. More specifically, the processor searches the computerized storage medium for the data variables. Also, the interface can receive input from health care professionals and from the patient for the data variables.

The interface receives clinician preferences and patient preferences, and the processor customizes the wellness plan according to the clinician preferences and patient preferences. The patient preferences comprise the type of interactive calendar application preferred by the patient. Further, the processor restricts content access to the wellness plan and varies the level access restriction based on the type of interactive calendar application preferred by the patient.

An interactive calendar is also operatively connected to the processor. The interactive calendar provides the wellness plan to the patient. The interactive calendar obtains any missing data variables and the patient preferences from the calendar application or patient. The interactive calendar performs dependency checks upon addition of a new wellness plan or action. Further, the interactive calendar provides the patient a list of tasks. The processor receives feedback regarding completion of the tasks, and the processor updates the interactive calendar based on the feedback. The interface outputs reports regarding the status of the wellness plan based on the interactive calendar application and the feedback.

Thus, the embodiments herein provide tasks, reminders, and appointments automatically to patients (or their family) and provide clinicians a competitive market advantage. Secondly, the embodiments herein create a new and very simple communication channel between clinics and patients that can be monitored electronically to analyze compliance and trigger care coordinator time only when patient intervention is needed.

BRIEF DESCRIPTION OF THE DRAWINGS

The embodiments of the invention will be better understood from the following detailed description with reference to the drawings, which are not necessarily drawing to scale and in which.

DETAILED DESCRIPTION

The embodiments of the invention and the various features and advantageous details thereof are explained more fully with reference to the non-limiting embodiments that are illustrated in the accompanying drawings and detailed in the following description.

The present embodiments provide a method and system of utilizing routine electronic transmissions such as a clinician order entry (CPOE) order message to identify one of a number of pre-established templates to create an individualized wellness plan. A healthcare provider may use standardized "best practices" templates and/or create customized templates within a clinician order entry (CPOE) or similar application. A wellness plan is built from a template that bundles dated and dependency-aware tasks, reminders, and calendar appointments for a single person. Such a plan allows for input requirements. The input requirements may be searched for in the computerized system, in prior patient plan entries, or the user can be prompted to provide such entries (e.g., date of birth, date of last tetanus vaccination, etc.). The plan provides a description, a well-codified signature (for other plans to search/use) and a list of user options that may be available (e.g., enable 24 hour reminders, notify primary care provider (PCP) on incomplete, notify PCP on complete). The template is then rolled out in the individual's wellness plan calendar application. Individual entries remain logically tied to the original plan and can be affected by the other entries or other plans.

Figure 1:
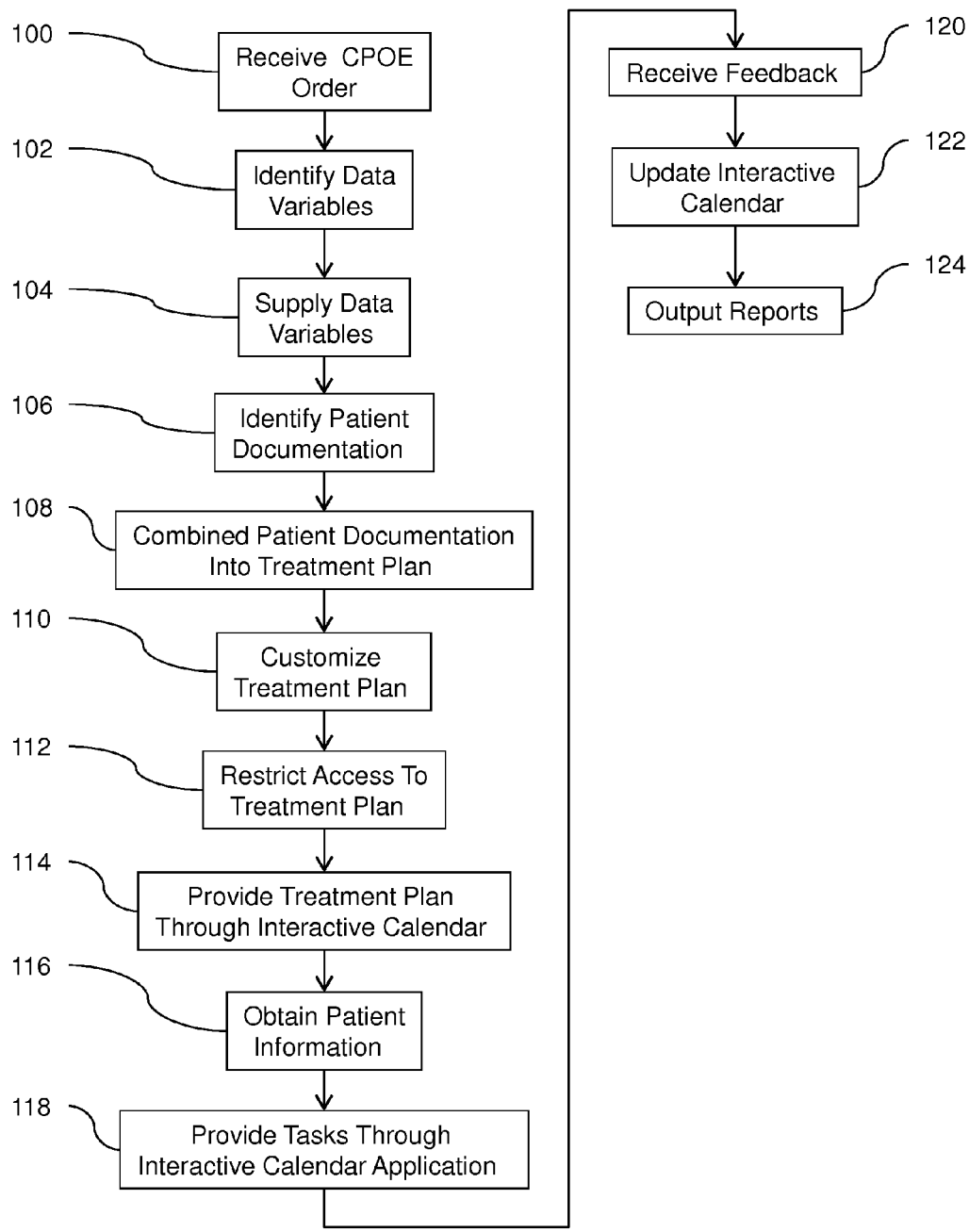
FIG. 1 is a block flow diagram illustrating an exemplary method embodiment herein.

As shown in flowchart form in FIG. 1, one embodiment herein comprises a computer-implemented method that receives, into a computerized system, at least one CPOE order relating to a patient (item 100). The order identifies a wellness plan that is based on one of a number of pre-established templates.

The method identifies data variables that need to be supplied for the wellness plan in item 102. The method supplies such data variables in item 104, using the computerized system, by searching databases for the data variables, receiving input from health care professionals for the data variables, and/or receiving input from the patient for the data variables.

In item 106, the method also identifies patient documentation related to the wellness plan, using the computerized system. The patient documentation comprises medical decision support documentation, patient educational documentation, contra-indication checks documentation (that check for medication conflicts), etc. The method then combines the patient documentation into the wellness plan in item 108.

The method can customize the wellness plan according to clinician preferences and patient preferences in item 110, and can restrict access and restrict content of the wellness plan in item 112, using the computerized system. The method receives the clinician preferences from health care professionals and receives the patient preferences from the patient. The patient preferences can include choices regarding the type of interactive calendar application preferred by the patient. Further, the level of content access restrictions to the wellness plan can be based on the type of interactive calendar application preferred by the patient.

In item 114, the method provides the wellness plan to the patient through an interactive calendar application and, in item 116, obtains patient information such as the data variables and the patient preferences from the patient through the interactive calendar application, using the computerized system. The interactive calendar performs dependency checks upon addition of the new wellness plan (ex software check for medication conflicts). This allows the method to provide the patient a list of tasks through the interactive calendar application in item 118, using the computerized system.

To track the success of the wellness plan, the method receives feedback regarding completion of the tasks from the user, the treatment provider, the pharmacy, or other entities, again using the computerized system, in item 120. Further, in item 122, the method updates the interactive calendar based on the feedback and, in item 124, can output reports regarding the status of the wellness plan based on the interactive calendar application and the feedback (using the computerized system) to both the clinician and the patient.

Thus, stated succinctly the embodiments herein provide a method for bi-directional communication of CPOE data to a patient by receiving pre-defined healthcare data (can be in HL7 format) from a data repository using a computer; extracting required healthcare data variables from the pre-defined healthcare data; extracting documentation (comprising decision support documentation, education documentation, and contra-indication check documentation) from module templates based on patient data; integrating the documentation with the required healthcare data variables to provide integrated data; customizing the integrated data based on clinician, patient, and health care practice preferences to provide customized integrated data; restricting access to the customized integrated data to provide a necessary level of security using the computer, the necessary level of security being based on a type of system access used by the patient; packaging the customized integrated data with healthcare tasks, reminders, and appointments specific to the patient to provide customized integrated data; and uploading the customized integrated data to a patient calendar application using the computer. The customized integrated data in the patient calendar application is viewed by the patient as an interactive calendar. Search criteria can be applied to the patient calendar application to search for the required healthcare data variables and dependencies are identified. The patient calendar application can prompt the patient to input the required healthcare data variables into the patient calendar application. Further, the patient calendar application can notify the patient of the healthcare tasks, reminders, appointments, and scripts. Scripts enable dependency-awareness such as triggering events such when a plan is completed, a plan is overridden by a new wellness plan, or a new medication is added that is contra-indicated with current medications.

Figure 2:
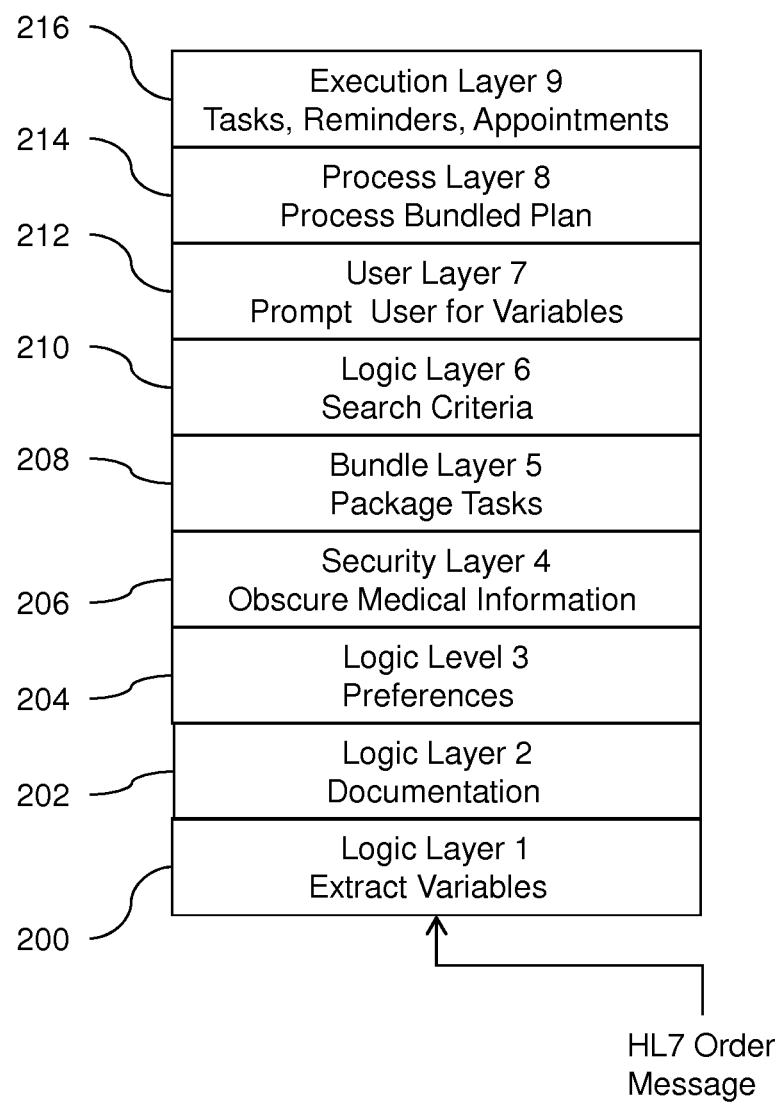
FIG. 2 is a logical/process diagram illustrating embodiments herein.

FIG. 2 is a logic/process diagram illustrating embodiments herein. This diagram obtains HL7 messages for orders, schedules (or proprietary form of these healthcare events), pre-defined templates, etc. for the logic layer 1 (item 200) which extracts variables that may need to be applied (e.g., a start date that is relative to a particular event). HL7 orders and schedules will be mainly complete entries; however, there may be times (especially if taking a pre-defined "best practice" template) that requires additional pieces of information such as the patient's date of birth, a start date for some therapy (example post-surgery), or preferred location info. Sometimes this information will be readily available from the healthcare systems generating these messages or plans. Other times the patient may need to specify the information in order to apply the plan in their calendar application. In this stage 200 these unknowns are obtained if possible, or identified for future query.

Item 202 illustrates logic layer 2, which uses decision support, document patient education and contra-indication checks. Providing materials to patients following a visit is increasingly important to providers. The materials provided in logic layer 2 give patients the ability to review instructions without time constraints and may give them time to realize they indeed have a contra-indication they had not discussed at the appointment, or additional questions that need answers. Often these instructions 202 are maintained within the module templates that are easily assembled for the patient's particular situation. Adding decision support documentation for patients is important for quality of care and compliance. The documentation supplied 202 could, for example, be used to discuss common arguments against immunizations, or the dangers of not completing an antibiotic medication.

Item 204 illustrates logic layer 3, which uses preferences/configuration set options and defines any user options (e.g., trigger message to clinics on completion). Logic layer 3 allows customization according to clinician, practice, and patient preferences. This functionality defines the desired interaction of tasks, reminders, and calendar events. For example, a clinician practice that is not tracking compliance for certain plans will prefer not to receive feedback. Patient preferences include what calendar they want to use—a calendar of theirs versus a patient portal calendar that is behind the healthcare provider's firewall. Many configuration options are available here.

Item 206 illustrates a security layer 4. The level of security can depend on, for example, user calendar selection (corporate hosted, software as a service hosted, or local "desktop" calendar) and the security layer 4 can obscure medical information behind login access. Depending on the calendar system in use, the bundled plan may be restricted in functionality and medical information visibility (i.e., use a link to a web site login vs. straight text). If the calendar is hosted, obscuring patient medical information is paramount to acceptance in security layer 4. Various encryption or external resource options exist to provide the necessary level of security depending on the type of calendar system in use by the patient.

In bundle layer 5 (item 208) all tasks, reminders, appointments, and scripts are packaged together. The bundle is then uploaded to the patient's interactive calendar application. Logic layer 6 (item 210) applies search criteria to the calendar application looking for defined variables that are needed as identified above by logic layer 1. In user layer 7 (item 212) the user is prompted for any outstanding variables, user options, etc. In the process layer 8 (item 214), the bundled plan is processed to show any lists of additions, deletions, warnings, dependencies, etc. caused by the plan. The process layer 8 also provides an accept/reject option before the upload to the interactive calendar. Finally, in layer 9 (item 216), the tasks, reminders, appointments, etc. (user action (or inaction)) are uploaded to the calendar application to run the plan logic bundle and to take the specified action.

Figure 3:
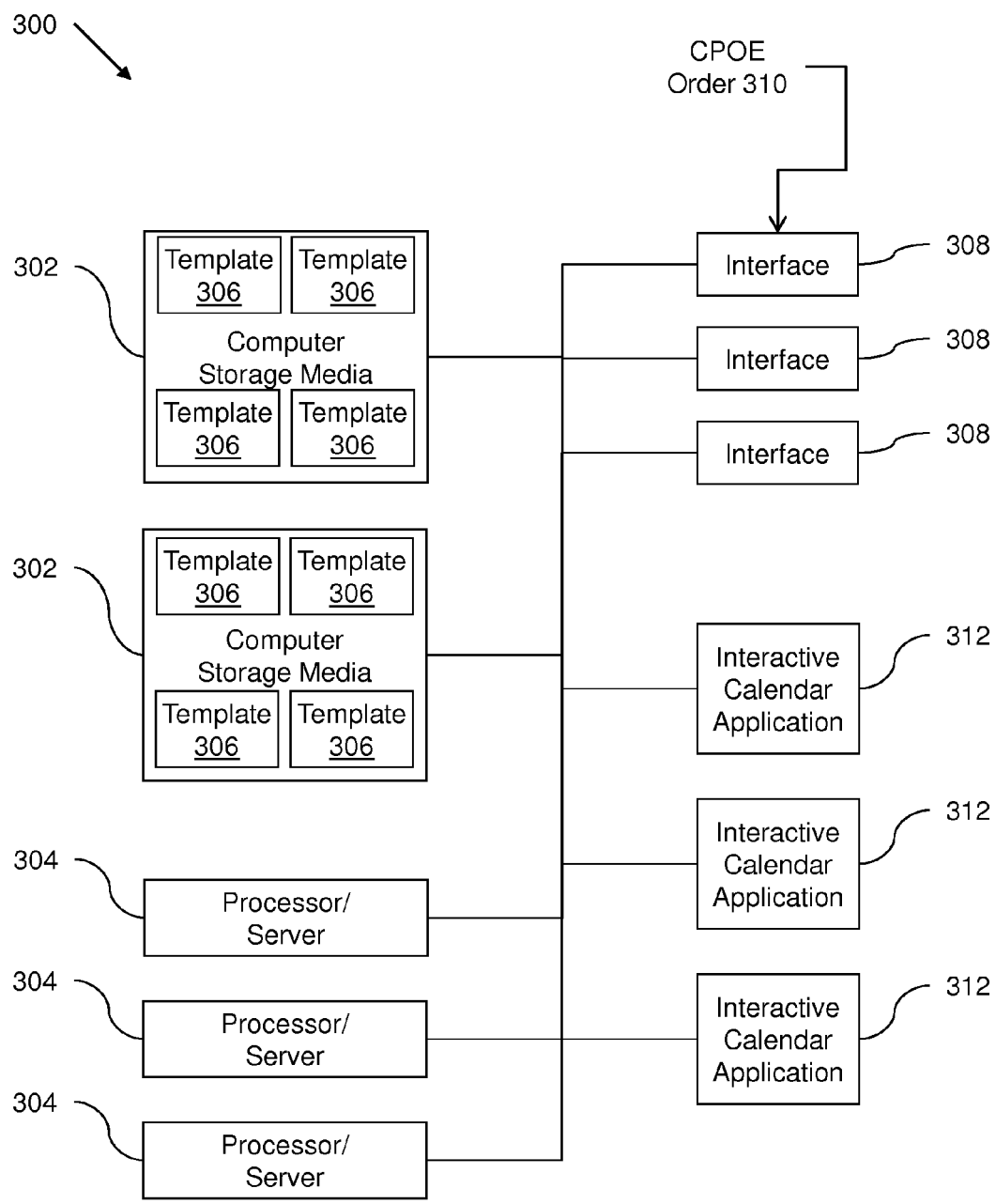
FIG. 3 is a schematic system diagram illustrating an exemplary system embodiment herein.

FIG. 3 illustrates an exemplary system embodiment that includes a computerized system 300 for processing clinician order entry (CPOE) orders. The system has at least one computerized storage medium 302 (floppy drives, hard drives, hard disks, optical storage, magnetic storage, etc.) operatively connected to at least one processor/server 304. Many such storage devices and processors/servers are commercially available from corporations such as International Business Machine Corporation located in Armonk, N.Y., USA and the details of such devices are not discussed herein. The computerized storage medium(s) 302 stores a plurality of pre-established templates 306. Each of the templates 306 comprises a wellness plan, and each wellness plan comprises dated and dependency-aware tasks, reminders, and calendar appointments, etc.

Each of the templates 306 further identifies patient documentation related to the wellness plan. The patient documentation comprises medical decision support documentation, patient educational documentation, contra-indication checks documentation, etc.

At least one interface 308 is operatively connected to the processor(s) 304. The interface(s) 308 can comprise a wired or wireless network connection (or other similar computer-to-computer connection) and/or a graphic user interface (keyboard, pointing device, touchpad, display device, etc.). The interface(s) 308 receives a CPOE order 310 relating to a patient. The order 310 identifies or is used to identify a wellness plan that is based on one of the pre-established templates 306. The processor 304 identifies data variables that need to be supplied for the wellness plan. More specifically, the processor 304 searches the computerized storage medium 302 for the data variables. Also, the interface 308 can receive input from health care professionals and from the patient for the data variables.

The interface 308 receives clinician preferences and patient preferences, and the processor 304 customizes the wellness plan according to the clinician preferences and patient preferences. The patient preferences comprise the type of interactive calendar application preferred by the patient. Further, the processor 304 restricts content access to the wellness plan and varies the level access restriction based on the type of interactive calendar application preferred by the patient.

At least one interactive calendar application 312 is also operatively connected to the processor 304. Many different calendar applications are commercially available from corporations such as Microsoft Corp., Redmond Wash., USA and Lotus Software Products available from International Business Machine Corporation, Armonk, N.Y., USA and the details of such calendar applications are not discussed at length herein. The invention embodied herein includes feature/module additions to interactive calendar applications to realize the dependency-aware and feedback capabilities within wellness plans. The interactive calendar application 312 provides the wellness plan to the patient. The interactive calendar application 312 obtains the data variables and the patient preferences from the patient. Further, the interactive calendar application 312 provides the patient a list of tasks. The processor 304 receives feedback regarding completion of the tasks, and the processor 304 updates the interactive calendar application 312 based on the feedback. The interface 308 outputs reports regarding the status of the wellness plan based on the interactive calendar application 312 and the feedback.

Thus, the embodiments herein provide tasks, reminders, and appointments automatically to patients (or their family) and provide clinicians a competitive market advantage. Secondly, the embodiments herein create a new and very simple communication channel between clinics and patients that can be monitored electronically to analyze compliance and trigger care coordinator time only when patient intervention is needed.

The following examples illustrate some operations of embodiments herein. In one example, a physical therapy plan may create 5 entries. The first two entries may have been completed, but the third entry may be dismissed by the individual. In this case a message would be automatically sent to the person's health clinic by embodiments herein for follow-up, and subsequent therapy entries could be removed. If this third entry is completed three days late, the subsequent two entries could then be enabled and shifted according to the original template specification.

In another example, a flu clinic plan creates 3 entries. If the first entry is missed by the person, but the second entry is marked as being completed, embodiments herein could direct a message to the person's health clinic for documentation of delivery of the flu vaccine and delete the third entry. The health clinic can follow-up individually with high-risk persons that have not gotten their vaccine after the third clinic day to schedule individual appointments or provide vaccination vouchers for a local pharmacy.

With embodiments herein, a new medication plan can overrides a previous medication plan by disabling the remaining medication events and creating 30 entries for the new medicine, along with a reminder event to call the health clinic to discuss how the new medication is working and obtain a refill if needed. This plan could also contain a contra-indication list that is checked against current medicine plans in the individual's calendar before changes are made. If the ordering clinician is different, a message can be sent to the prior clinician noting the change in medication for that patient.

In a further example of embodiments herein, a pediatric wellness and vaccination plan can be provided at birth to the new parents. During the first two years of events, all is followed or completed with health clinic reminders. If they are then diagnosed with autism, a new plan specific to others diagnosed with this level of autism could be issued that overrides the original wellness plan. Additional plan overrides can be provided based on their needs.

An additional example of operations of embodiments herein occurs where a laboratory visit is ordered to obtain a patient's fasting glucose and cholesterol. A plan would be created that has evening fasting reminders & morning reminders including directions to a laboratory near the patient's work location. Once the task is marked complete, a reminder is added to the patient's calendar to check back for results in 1 week and the clinician is notified.

The embodiments of the invention can take the form of an entirely hardware embodiment, an entirely software embodiment or an embodiment including both hardware and software elements. In a preferred embodiment, the invention is implemented in software, which includes but is not limited to firmware, resident software, microcode, etc.

Furthermore, the embodiments of the invention can take the form of a computer program product accessible from a computer-usable or computer-readable medium providing program code for use by or in connection with a computer or any instruction running system. For the purposes of this description, a computer-usable or computer readable medium can be any apparatus that can comprise, store, communicate, propagate, or transport the program for use by or in connection with the instruction running system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual running of the program code, bulk storage, and cache memories which provide temporary storage of at least some program code in order to reduce the number of times code must be retrieved from bulk storage during running.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening firewalled or public networks. Modems, cable modem and Ethernet cards are just a few of the currently available types of network adapters.

Figure 4:
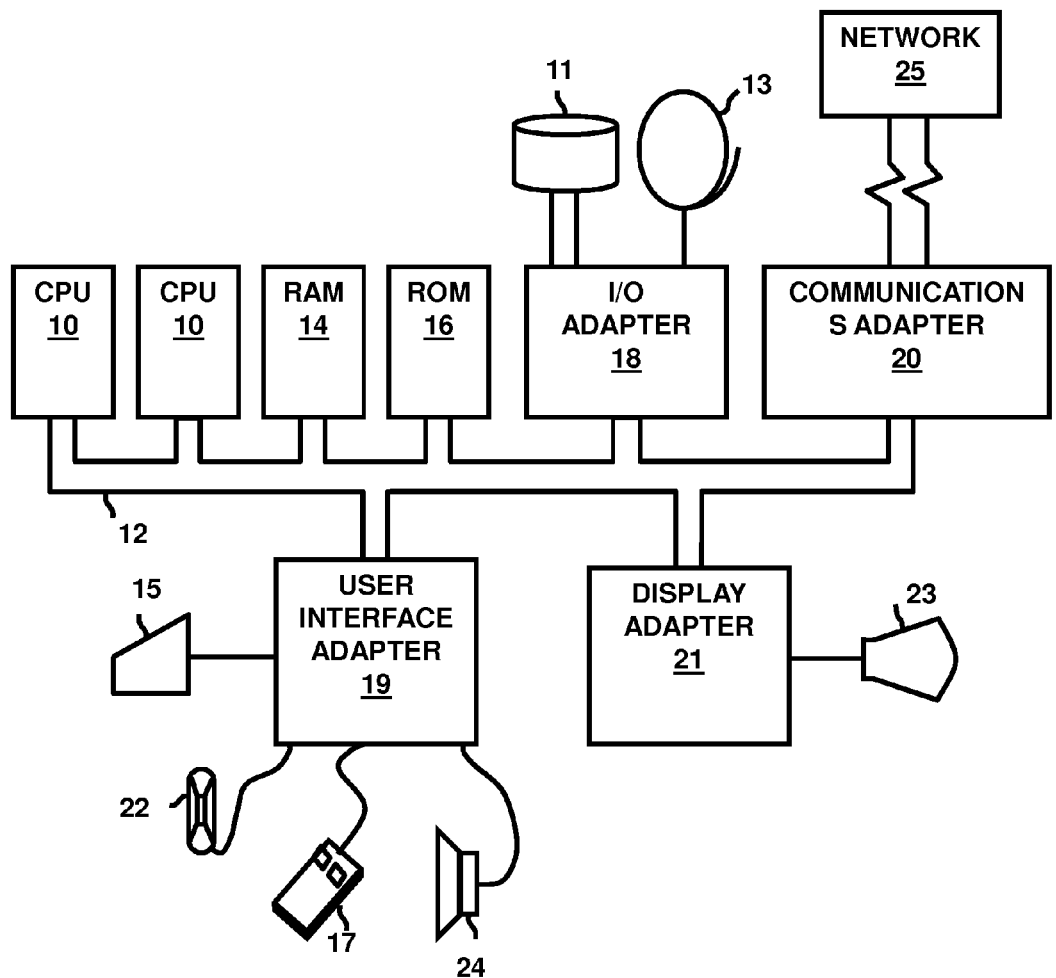
FIG. 4 is a schematic diagram illustrating an exemplary hardware environment that can be used to implement the embodiments of the invention.

A representative hardware environment for practicing the embodiments of the invention is depicted in FIG. 4. This schematic drawing illustrates a hardware configuration of an information handling/computer system in accordance with the embodiments of the invention. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to run the methodology of the embodiments of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

It should be understood that the corresponding structures, materials, acts, and equivalents of all means or step plus function elements in the claims below are intended to include any structure, material, or act for performing the function in combination with other claimed elements as specifically claimed. Additionally, it should be understood that the above-description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. Well-known components and processing techniques are omitted in the above-description so as to not unnecessarily obscure the embodiments of the invention.

Finally, it should also be understood that the terminology used in the above-description is for the purpose of describing particular embodiments only and is not intended to be limiting of the invention. For example, as used herein, the singular forms "a", "an" and "the" are intended to include the plural forms as well, unless the context clearly indicates otherwise. Furthermore, as used herein, the terms "comprises", "comprising," and/or "incorporating" when used in this specification, specify the presence of stated features, integers, steps, operations, elements, and/or components, but do not preclude the presence or addition of one or more other features, integers, steps, operations, elements, components, and/or groups thereof.

What is claimed is:

1. A computer-implemented method comprising:
receiving, into a computerized system, a clinician order entry (CPOE) order relating to a patient, said order identifying a wellness plan that is based on one of a number of pre-established templates;
identifying data variables that need to be supplied for said wellness plan, using said computerized system;
identifying patient documentation related to said wellness plan, using said computerized system;
combining said patient documentation into said wellness plan, using said computerized system;
customizing said wellness plan according to clinician preferences and patient preferences regarding a type of interactive calendar application preferred by said patient, using said computerized system;
obtaining said data variables and said patient preferences from said patient through said interactive calendar application, using said computerized system;
restricting access to said wellness plan based on said type of interactive calendar application preferred by said patient, using said computerized system;
providing said wellness plan to said patient through said interactive calendar application, using said computerized system;
providing said patient a list of required tasks through said interactive calendar application, using said computerized system;
receiving feedback from said patient regarding completion of said required tasks, using said computerized system;
updating said interactive calendar based on said feedback, using said computerized system; and
outputting reports regarding a status of said wellness plan based on said interactive calendar application and said feedback, using said computerized system, to said patient and a clinician.

2. The method according to claim 1, further comprising supplying said data variables, using said computerized system, by at least one of:
searching databases for said data variables;
receiving input from health care professionals for said data variables; and
receiving input from said patient for said data variables.

3. The method according to claim 1, said patient documentation comprising medical decision support documentation, patient educational documentation, and contra-indication checking documentation.

4. The method according to claim 1, further comprising receiving said clinician preferences from health care professionals and receiving said patient preferences from said patient.

5. A computerized system for processing clinician order entry (CPOE) orders, said system comprising:
a memory that stores a clinician order entry (CPOE) order relating to a patient, and a patient preference regarding a type of interactive calendar application preferred by said patient; and
a processor that performs:
receiving a clinician order entry (CPOE) order relating to a patient, said order identifying a wellness plan that is based on one of a number of pre-established templates;
identifying data variables that need to be supplied for said wellness plan;
identifying patient documentation related to said wellness plan;
combining said patient documentation into said wellness plan;
customizing said wellness plan according to clinician preferences and patient preferences regarding a type of interactive calendar application preferred by said patient;
obtaining said data variables and said patient preferences from said patient through said interactive calendar application;
restricting access to said wellness plan based on said type of interactive calendar application preferred by said patient;
providing said wellness plan to said patient through said interactive calendar application;
providing said patient a list of required tasks through said interactive calendar application;
receiving feedback from said patient regarding completion of said required tasks;
updating said interactive calendar based on said feedback; and
outputting reports regarding a status of said wellness plan, based on said interactive calendar application and said feedback, to a patient and a clinician.

6. A non-transitory computer program storage medium tangibly embodying instructions executable by a computer to perform a computer-implemented method comprising:
receiving a clinician order entry (CPOE) order relating to a patient, said order identifying a wellness plan that is based on one of a number of pre-established templates;
identifying data variables that need to be supplied for said wellness plan;

identifying patient documentation related to said wellness plan; combining said patient documentation into said wellness plan;

customizing said wellness plan according to clinician preferences and patient preferences regarding a type of interactive calendar application preferred by said patient;

obtaining said data variables and said patient preferences from said patient through said interactive calendar application;

restricting access to said wellness plan based on said type of interactive calendar application preferred by said patient;

providing said wellness plan to said patient through said interactive calendar application;

providing said patient a list of required tasks through said interactive calendar application;

receiving feedback from said patient regarding completion of said required tasks;

updating said interactive calendar based on said feedback; and outputting reports regarding a status of said wellness plan, based on said interactive calendar application and said feedback, to said patient and a clinician.

7. The tangible computer program storage medium according to claim 6, said method further comprising supplying said data variables, using said computerized system, by at least one of:

searching databases for said data variables;

receiving input from health care professionals for said data variables; and receiving input from said patient for said data variables.

8. The tangible computer program storage medium according to claim 6, said patient documentation comprising medical decision support documentation, patient educational documentation, and contra-indication checking documentation.

9. The non-transitory computer program storage medium according to claim 6, said patient preferences comprising the type of interactive calendar application preferred by said patient.

10. The tangible computer program storage medium according to claim 6, said method further comprising receiving said clinician preferences from health care professionals and receiving said patient preferences from said patient.

* * * * *